(12) United States Patent
Dong (10) Patent No.: US 11,270,794 B2
(45) Date of Patent: Mar. 8, 2022

(54) TELEMEDICINE DEVICE, INFORMATION ACQUIRING DEVICE, AND TELEMEDICINE SYSTEM AND METHOD

(71) Applicant: BOE TECHNOLOGY GROUP CO., LTD., Beijing (CN)

(72) Inventor: Wenchu Dong, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 168 days.

(21) Appl. No.: 16/089,625

(22) PCT Filed: Jan. 11, 2018

(86) PCT No.: PCT/CN2018/072177
§ 371 (c)(1),
(2) Date: Sep. 28, 2018

(87) PCT Pub. No.: WO2019/000909
PCT Pub. Date: Jan. 3, 2019

(65) Prior Publication Data
US 2019/0378614 A1    Dec. 12, 2019

(30) Foreign Application Priority Data

Jun. 29, 2017    (CN) .......................... 201710515868.9

(51) Int. Cl.
*G16H 40/67*    (2018.01)
*G16H 20/00*    (2018.01)
(Continued)

(52) U.S. Cl.
CPC ........... *G16H 40/67* (2018.01); *A61B 5/0002* (2013.01); *G16H 20/00* (2018.01); *G16H 80/00* (2018.01); *A61B 5/02* (2013.01)

(58) Field of Classification Search
CPC ........ G16H 40/67; G16H 20/00; G16H 80/00; A61B 5/0002; A61B 5/02
(Continued)

(56) References Cited

U.S. PATENT DOCUMENTS

2004/0097836 A1\* 5/2004 Ombrellaro ............ A61B 8/565
600/587
2012/0139731 A1\* 6/2012 Razoumov .............. G16Z 99/00
340/573.1
(Continued)

FOREIGN PATENT DOCUMENTS

CN    1895163 A    1/2007
CN    101019763 A    8/2007
(Continued)

OTHER PUBLICATIONS

Abo-Zahhad, M et al. "A wireless emergency telemedicine system for patients monitoring and diagnosis." International journal of telemedicine and applications vol. 2014 (2014): 380787. doi:10.1155/2014/380787 (Year: 2014).\*

(Continued)

*Primary Examiner* — Christopher L Gilligan
*Assistant Examiner* — Bennett Stephen Erickson
(74) *Attorney, Agent, or Firm* — Dilworth & Barrese, LLP.; Michael J. Musella, Esq.

(57) ABSTRACT

A telemedicine device, communicated with a telemedicine information acquiring device, includes a communication unit and an operation unit. The communication unit is configured to communicate with the telemedicine information acquiring device, and receive physiological sign information of a patient from the telemedicine information acquiring device. The operation unit is configured to restore at least part of the physiological sign information according to the physiological sign information received by the com- (Continued)

munication unit. Also are provided a telemedicine information acquiring device and a telemedicine method.

15 Claims, 3 Drawing Sheets

(51) Int. Cl.
*G16H 80/00* (2018.01)
*A61B 5/02* (2006.01)
*A61B 5/00* (2006.01)

(58) Field of Classification Search
USPC .............................................................. 705/2
See application file for complete search history.

(56) References Cited

U.S. PATENT DOCUMENTS

| | | | | |
|---|---|---|---|---|
| 2012/0223823 | A1* | 9/2012 | Dunko | A61B 5/7465 340/407.1 |
| 2015/0339570 | A1* | 11/2015 | Scheffler | G06N 3/04 706/16 |
| 2017/0020441 | A1* | 1/2017 | Flitsch | A61B 5/1112 |
| 2017/0156662 | A1* | 6/2017 | Goodall | A61B 5/0036 |
| 2017/0296056 | A1* | 10/2017 | Hresko | G16H 40/63 |
| 2017/0372639 | A1* | 12/2017 | Cowperthwait | G16H 20/40 |
| 2018/0036531 | A1* | 2/2018 | Schwarz | A61N 1/0484 |
| 2018/0116597 | A1* | 5/2018 | Yu | A61B 5/0245 |

FOREIGN PATENT DOCUMENTS

| | | |
|---|---|---|
| CN | 101606840 A | 12/2009 |
| CN | 201710478 U | 1/2011 |
| CN | 103169458 A | 6/2013 |
| CN | 103876713 A | 6/2014 |
| CN | 104083156 A | 10/2014 |
| CN | 104825142 A | 8/2015 |
| CN | 204971241 U | 1/2016 |
| CN | 105433914 A | 3/2016 |
| CN | 205054186 U | 3/2016 |
| WO | 2004091378 A2 | 10/2004 |

OTHER PUBLICATIONS

First Chinese Office Action in priority Chinese Patent Application No. 201710515868.9 dated Aug. 7, 2020.
Indian Office Action from Indian Patent Application No. 201817036945 dated Nov. 25, 2020.
Extended European Search Report from European Patent Application No. 18769940.0 dated Dec. 9, 2020.
International Search Report and Writen Opinion dated Apr. 18, 2018.
European Office Action from European Patent Application No. 18769940.0 dated Aug. 31, 2021.
Cockburn et al., "A review of Overview + Detail, Zooming, and Focus + Context Interfaces", ACM Computing Surveys, vol. 41, Dec. 2008, pp. 1-31.

* cited by examiner

TELEMEDICINE DEVICE, INFORMATION ACQUIRING DEVICE, AND TELEMEDICINE SYSTEM AND METHOD

The application claims priority to the Chinese patent application No. 201710515868.9, filed on Jun. 29, 2017, the entire disclosure of which is incorporated herein by reference as part of the present application.

TECHNICAL FIELD

Embodiments of the present disclosure relate to a telemedicine device, a telemedicine information acquiring device, and a telemedicine method.

BACKGROUND

With increasing demand for telemedicine, doctors or patients pose higher and higher requirements on experiences in terms of telemedicine devices, information availability, and diagnostic efficiency and so on.

However, in traditional Chinese medicine, doctors often need to see a current state of a patient's face and feel the patient's pulse, so as to know condition of the patient, due to importance of the doctors' experiences and four diagnostic techniques such as looking the appearance, listening to the sound, inquiring for the condition and touching for the type of pulse; however, most of existing telemedicine devices are for Western medicine, which may not effectively access to information such as current state of a patient's face, and may not accurately acquire pulse information, so that the existing telemedicine devices are not suitable for traditional Chinese medicine therapy.

SUMMARY

At least an embodiment of the present disclosure provides a telemedicine device, communicated with a telemedicine information acquiring device, the telemedicine device comprises: a communication unit and an operation unit, the communication unit is configured to communicate with the telemedicine information acquiring device, and receive physiological sign information of a patient from the telemedicine information acquiring device; and the operation unit is configured to restore at least part of the physiological sign information according to the physiological sign information received by the communication unit.

For example, the operation unit includes a pulse restoring unit and the physiological sign information includes pulse information, the communication unit is configured to receive a pulse signal indicating pulse information of the patient from the telemedicine information acquiring device; and the pulse restoring unit is configured to restore the pulse signal, so as to restore pulse of the patient.

For example, the pulse restoring unit includes a vibrating portion, the vibrating portion is configured to vibrate according to the received pulse signal.

For example, the vibrating portion is a Micro Electro Mechanical Systems based vibration sensor.

For example, the pulse restoring unit further includes a touch region, the touch region being provided with artificial human skin.

For example, the telemedicine device further comprises a display unit, the communication unit receiving pulse information of the patient from the telemedicine information acquiring device, and the display unit is configured to display a waveform diagram of the pulse information in the physiological sign information.

For example, the physiological sign information includes a body feature image, the communication unit being further configured to receive the body feature image of the patient from the telemedicine information acquiring device, and the display unit is configured to display the body feature image.

For example, the display unit includes a first display region and a second display region, the first display region is configured to display an overall image of the body feature image, and the second display region is configured to display an enlarged image of at least a part of the body feature image.

For example, the operation unit further includes a function switching device, the function switching device switching contents displayed by the first display region and the second display region according to a user instruction.

For example, the telemedicine device further comprises a speaker, the communication unit being further configured to receive sound information of the patient from the telemedicine information acquiring device, and the speaker is configured to output the sound information.

At least an embodiment of the present disclosure provides a telemedicine information acquiring device, communicated with a telemedicine device, the telemedicine information acquiring device comprises: a communication unit and a physiological sign information acquiring unit, the physiological sign information acquiring unit is configured to acquire physiological sign information of a patient, and the communication unit is configured to communicate with the telemedicine device, and transmit the physiological sign information to the telemedicine device.

For example, the physiological sign acquiring unit includes a physical sign detecting sleeve, for being worn on a limb of the patient and acquiring pulse information of the patient.

For example, the pulse information includes at least one of a vibration amplitude and a vibration frequency.

For example, the physical sign detecting sleeve includes a signal amplifier, configured to amplify a pulse signal indicating the pulse information.

For example, the physiological sign information acquiring unit further includes a fingerprint identifying unit, configured to acquire fingerprint information of the patient.

For example, the device further comprises a chair, the physiological sign information acquiring unit being arranged on an armrest of the chair.

For example, the physiological sign information acquiring unit includes an image acquiring unit, the image acquiring unit is configured to acquire a body feature image of the patient.

For example, the image acquiring unit includes a first camera and a second camera, the first camera being used for acquiring a half body or a whole body image of the patient, and the second camera being used for acquiring an image of a first part of the body of the patient.

For example, the device further comprises a voice input device, configured to input voice by the patient.

At least an embodiment of the present disclosure provides a telemedicine system, comprising a telemedicine device and the telemedicine information acquiring device; the telemedicine device being communicated with the telemedicine information acquiring device, and the telemedicine device including a communication unit and an operation unit, the communication unit is configured to communicate with the telemedicine information acquiring device, and receive physiological sign information of the patient from the telemedicine information acquiring device; the operation unit is configured to restore at least part of the physiological sign information according to the physiological sign information received by the communication unit.

At least an embodiment of the present disclosure provides a telemedicine system, comprising the telemedicine device and a telemedicine information acquiring device; the telemedicine information acquiring device, communicated with the telemedicine device, and the telemedicine information acquiring device including a communication unit and a physiological sign information acquiring unit; the physiological sign information acquiring unit is configured to acquire physiological sign information of the patient; the communication unit is configured to communicate with the telemedicine device, and transmit the physiological sign information to the telemedicine device.

At least an embodiment of the present disclosure provides a telemedicine method, comprising: acquiring physiological sign information of a patient by a telemedicine information acquiring device; transmitting the physiological sign information to a telemedicine device by the telemedicine information acquiring device; receiving the physiological sign information by the telemedicine device; and restoring the received physiological sign information by the telemedicine device.

For example, the physiological sign information includes pulse information, acquiring pulse information of the patient by the telemedicine information acquiring device; transmitting a pulse signal indicating the pulse information to the telemedicine device by the telemedicine information acquiring device; receiving the pulse signal by the telemedicine device; and restoring the received pulse signal to simulate pulse information of the patient by the telemedicine device.

For example, the physiological sign information further includes a body feature image, acquiring a body feature image of the patient by the telemedicine information acquiring device; transmitting the body feature image to the telemedicine device by the telemedicine information acquiring device; receiving the body feature image by the telemedicine device; and displaying the received body feature image by the telemedicine device.

For example, the method further comprises: acquiring identity information of the patient by the telemedicine information acquiring device; transmitting the identity information to the telemedicine device by the telemedicine information acquiring device; receiving the identity information by the telemedicine device; and verifying the patient according to the received identity information by the telemedicine device.

BRIEF DESCRIPTION OF THE DRAWINGS

In order to clearly illustrate the technical solution of the embodiments of the present disclosure, the drawings of the embodiments will be briefly described in the following; the described drawings are only related to some embodiments of the present disclosure.

DETAILED DESCRIPTION

Hereinafter, preferred embodiments of the present disclosure will be described in detail with reference to the accompanying drawings. It should be noted that, in the specification and the accompanying drawings, steps and elements which are substantially same are denoted by the same reference signs, and repeated explanations of these steps and elements will be omitted.

In the following embodiments of the present disclosure, a telemedicine device may be a doctor-side device, for example, an electronic device for performing diagnostic analysis on a patient. A telemedicine information acquiring device refers to a patient-side device, for example, an electronic device for acquiring physiological sign information of a patient. In the embodiments of the present disclosure, the telemedicine device and the telemedicine information acquiring device may be in different places and may perform remote communication, for example, signal connection between the two electronic devices, and telemedicine may be realized by remote communication through a network.

Figure 1:
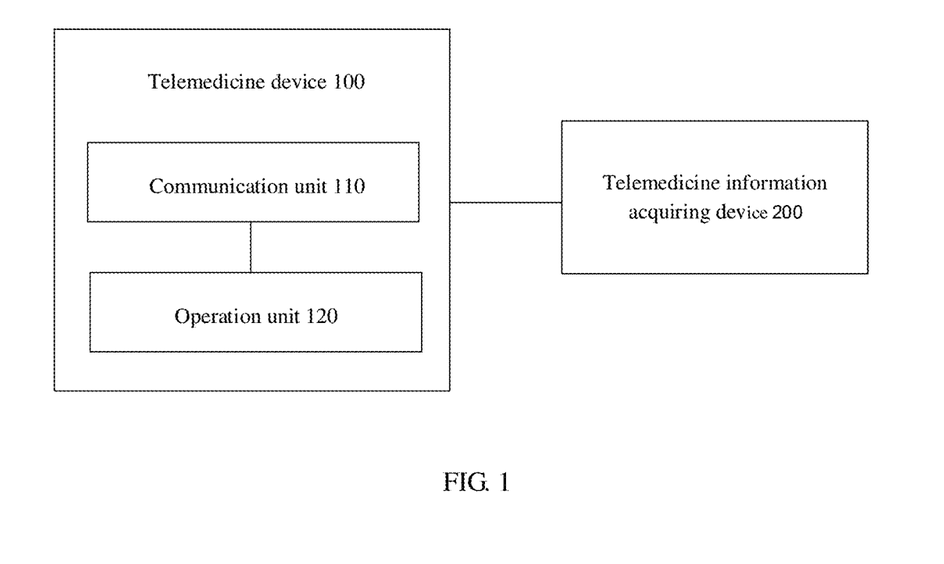
FIG. 1 shows a structural schematic diagram of a telemedicine device according to an embodiment of the present disclosure.

FIG. 1 shows a structural schematic diagram of a telemedicine device according to an embodiment of the present disclosure. Referring to FIG. 1, the telemedicine device 100 comprises a communication unit 110 and an operation unit 120. The communication unit 110 is configured to communicate with a telemedicine information acquiring device 200 and receive physiological sign information of a patient from the telemedicine information acquiring device 200. The communication unit 110 includes, for example, an antenna unit, a modem, a network adapter, a router and the like. The telemedicine device 100 may communicate with the telemedicine information acquiring device 200 in a wired manner, or may communicate with the telemedicine information acquiring device 200 in a wireless manner. The operation unit 120 is configured to restore at least part of the physiological sign information according to the physiological sign information received by the communication unit 110. The operation unit 120 is, for example, a platform for operating by a doctor, such as a console, a smart operating table, which is capable of processing a received signal indicating physiological sign of a patient to restore the signal to the physiological sign information or partial physiological sign information of the patient.

In the embodiment of the present disclosure, accurate and effective remote diagnosis in the traditional Chinese medicine may be realized by restoring the physiological sign information of the patient, thereby facilitating medical treatment for the patient.

Figure 2:
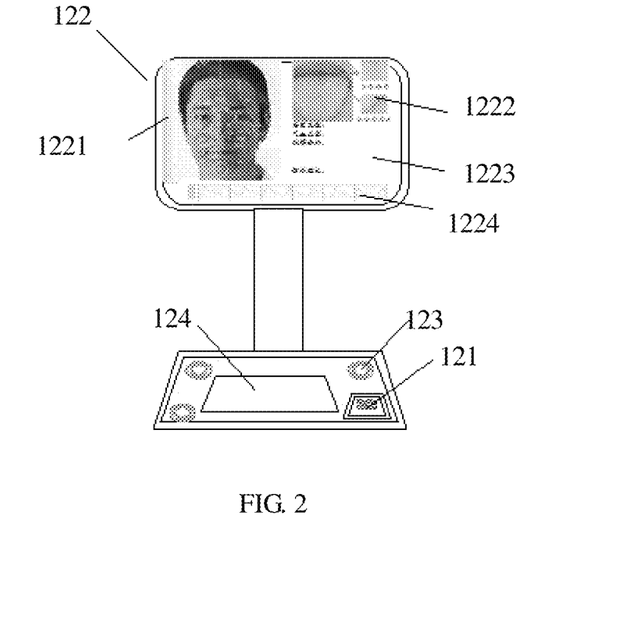
FIG. 2 shows an exemplary structural diagram of a telemedicine device according to an embodiment of the present disclosure.

FIG. 2 shows an exemplary structural diagram of a telemedicine device according to an embodiment of the present disclosure. Referring to FIG. 2, the operation unit 120 may include a pulse restoring unit 121. The communication unit 110 receives a pulse signal indicating pulse information of a patient from the telemedicine information acquiring device 200. And then, the pulse restoring unit may restore the received pulse signal, so as to restore pulse of the patient. For example, the pulse restoring unit 121 may include a vibrating component, after the telemedicine device 100 receives the signal indicating the pulse information of the patient, the signal passes through the vibrating component, and the vibrating component vibrates according to the received pulse signal. According to an example of the present disclosure, the vibrating component may be, for example, an optical sensor such as a Micro Electro Mechanical Systems (MEMS) based vibration sensor, or may also be a mechanical vibration sensor or an electrical sensor. For example, if the signal indicating the pulse information of the patient is an analog electric signal, the vibrating portion vibrates according to high level or low level of the analog electric signal. If the signal indicating the pulse information of the patient is a digital electrical signal, the signal may be converted into an analog electrical signal by a digital-to-analog converter at first and then transmitted to the vibrating portion to trigger vibrating. If the signal indicating the pulse information of the patient is an optical signal, the vibration may be detected by using a MEMS vibration sensor.

In addition, referring to FIG. 2, the pulse restoring unit 121 may further include a touch region, for touching by a doctor to sense the signal indicating the pulse information of the patient. In order to improve a pulse simulation effect, artificial human skin may be provided in the touch region, and therefore, when the doctor touches the touch region, it feels like diagnosing a real person. The artificial human skin may be made of, for example, a rubber material.

In addition, referring to FIG. 2, the operation unit 120 may further include a display unit 122, and the display unit may be, for example, a display screen. After the communication unit 110 receives the signal indicating the pulse information of the patient from the telemedicine information acquiring device, a waveform diagram of the pulse information may be further displayed on the display unit 122, for further use by a doctor as diagnostic reference.

In addition, in order to achieve the four diagnostic techniques such as looking the appearance, listening to the sound, inquiring for the condition and touching for the type of pulse on a patient, and know a body feature of the patient, the telemedicine device may further acquire a body feature image of the patient. For example, the communication unit receives the body feature image of the patient from the telemedicine information acquiring device, and the display unit displays according to the received body feature image. The body feature image includes, for example, a facial feature image, a tongue coating image, a lesion part image, a full-body image or a half-body image and the like. The telemedicine device may acquire an image of the image of the corresponding part of the patient according to an instruction of the doctor. For example, the doctor requests to acquire a tongue coating image of the patient; after the instruction is transmitted to the telemedicine information acquiring device through the communication unit, the telemedicine information acquiring device may control an image acquiring unit installed thereon to acquire the image of the corresponding part.

According to an example of the present disclosure, the display unit 122 may include a first display region 1221 and a second display region 1222. The first display region 1221 may display an overall image of the body feature image. The second display region 1222 may display an image of a certain portion of the body feature image, for example, an enlarged image of a certain portion. For example, referring to FIG. 2, the first display region 1221 displays an overall image of a face of a patient, while a second display region 1222 displays an enlarged image of tongue coating of the patient. In this way, a doctor may perform comprehensive analysis based on the facial feature image of the patient and the tongue coating image of the key part, so as to diagnose the patient. In addition, optionally, the second display region 1222 may not only display just one image, but also may display a plurality of images, for example, displaying enlarged images of different angles or different enlarged images of a certain part, etc.

In addition, the display unit 122 may further include a diagnostic analysis display region 1223 and a pulse waveform display region 1224. The diagnostic analysis display region 1223 is used for displaying result of analyzing the image according to a user instruction. The pulse waveform display region 1224 may display the waveform according to the received waveform information of the patient as reference for the doctor.

In addition, referring to FIG. 2, the operation unit 120 may further include a function switching device, for example, a function switching button 123, and the function switching button 123 may switch contents and display effects displayed on the first display region 1221 and the second display region 1222 according to an instruction input by a doctor.

In addition, referring to FIG. 2, the operation unit 120 may further include a keyboard region or a touch region 124, for the user to input information, control a cursor of the display unit 122 and the like.

In addition, the telemedicine device may also include a speaker, a microphone and the like. The communication unit is further configured to receive or transmit sound information from the telemedicine information acquiring device, and the microphone and the speaker are configured to input or output the sound information, so that a doctor may communicate with the telemedicine information acquiring device to know condition of the patient.

The telemedicine device in the embodiment of the present disclosure may remotely acquire patient information of a patient, which facilitates a doctor to remotely perform the four diagnostic techniques such as looking the appearance, listening to the sound, inquiring for the condition and touching for the type of pulse on a patient, effectively realizes remote diagnosis in the traditional Chinese medicine, and facilitates medical treatment for the user.

Figure 3:
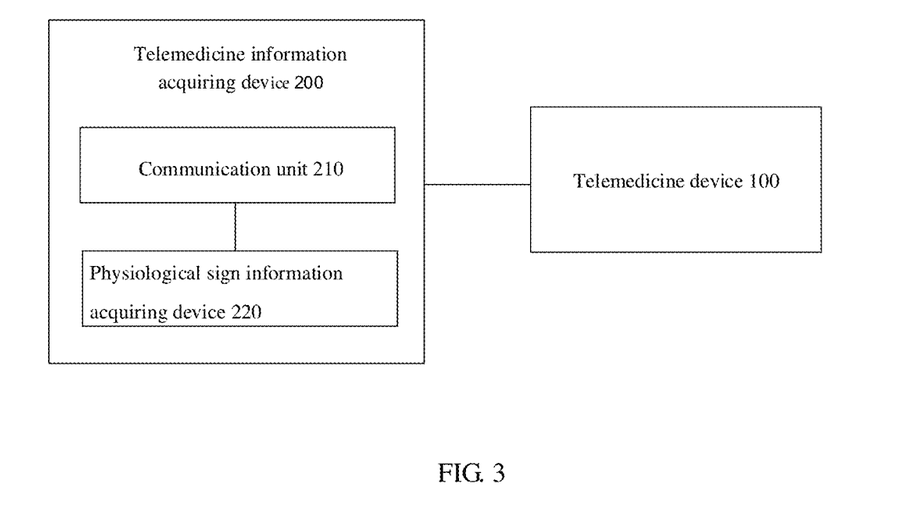
FIG. 3 shows a structural schematic diagram of a telemedicine information acquiring device according to an embodiment of the present disclosure.

Hereinbefore, the telemedicine device used in a doctor-side is introduced, and a patient-side telemedicine information acquiring device will be introduced in the following. FIG. 3 shows a structural schematic diagram of a telemedicine information acquiring device according to an embodiment of the present disclosure. Referring to FIG. 3, the telemedicine information acquiring device 200 is communicated with the telemedicine device 100. The telemedicine information acquiring device 200 includes a communication unit 210 and a physiological sign information acquiring unit 220. The physiological sign information acquiring unit 220 is configured to acquire physiological sign information of a patient. The physiological sign information is, for example, body posture, appearance, pulse, heart rate, lesion information and the like. The communication unit 210 is configured to communicate with the telemedicine device 100, and the communication unit 210 includes, for example, an antenna unit, a modem, a network adapter, a router and the like. Through the communication unit 210, the telemedicine information acquiring device 200 may communicate with the telemedicine device 100 in a wired or wireless method, and transmit the physiological sign information of the patient acquired by the physiological sign information acquiring unit 220 to the telemedicine device, so that the telemedicine device may restore the physiological sign information of the patient, to facilitate diagnosis of the doctor.

The telemedicine information acquiring unit in the embodiment of the present disclosure may accurately acquire the physiological sign information of the patient and transmit the information to the doctor for diagnosis, thereby realizing remote diagnosis in the traditional Chinese medicine.

Figure 4:
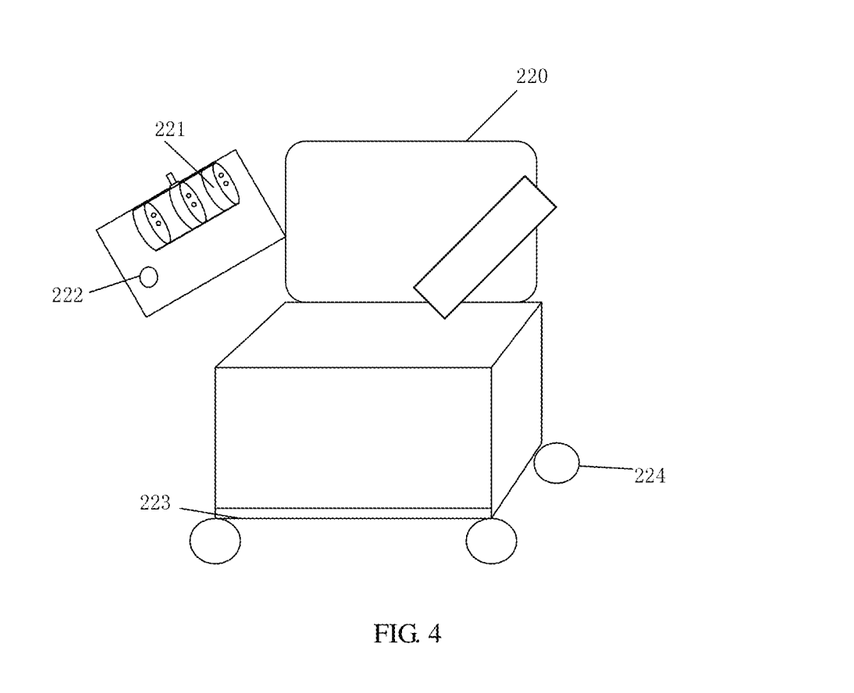
FIG. 4 shows an exemplary structural diagram of a telemedicine information acquiring device according to an embodiment of the present disclosure.

FIG. 4 shows an exemplary structural diagram of a telemedicine information acquiring device according to an embodiment of the present disclosure. Referring to FIG. 4, the physiological sign acquiring unit 220, for example, may be designed as a patient chair or a patient bed. The embodiment of the present disclosure is described by taking a chair as an example. Referring to FIG. 4, the patient chair may be provided with a physical sign detecting sleeve 221, and the physical sign detecting sleeve 221 may be worn on a limb of a patient to acquire pulse information of the patient. Optionally, the physical sign detecting sleeve 221 may be arranged on an armrest of the chair, and may be worn on a wrist, a finger or an arm of the patient after the patient sits down, to obtain the pulse information of the patient.

Figure 5:
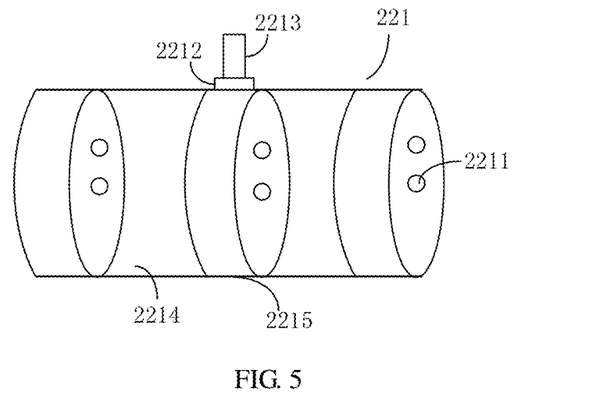
FIG. 5 shows an exemplary structural diagram of a physical sign detecting sleeve according to an embodiment of the present disclosure.

FIG. 5 shows an exemplary structural diagram of a physical sign detecting sleeve according to an embodiment of the present disclosure. Referring to FIG. 5, the physical sign detecting sleeve 221 is, for example, a wristlet including a fixing part 2214, which may fix the wristlet on a wrist of a user. For example, the wristlet may be fixed on the wrist of the user by a Velcro or an elastic band. The physical sign detecting sleeve 221 may further include one or a plurality of armlets 2215, arranged on an inner wall of the fixing part, and each armlet 2215 may be provided with a pulse sensor 2211, for acquiring pulse information. There may be one pulse sensor 2211 arranged in a position of a vein of the wrist of the patient. Optionally, there may also be a plurality of pulse sensors 2211 arranged in positions of venous blood vessels of the wrist and the arm.

According to an example of the present disclosure, the pulse sensor is, for example, a micro pressure sensor, and the sensor may be placed close to skin of a test point of a patient and convert pressure process in pulse beat into a signal to output, so that a detecting part may acquire a subtle process of pulse beat, and for example, a vibration amplitude and a vibration frequency of the pulse are acquired, thereby acquiring pulse information of the patient.

In addition, referring to FIG. 5, the physical sign detecting sleeve 221 may further include a signal amplifier 2212, for amplifying the pulse signal acquired by the pulse sensor, which is favorable for further signal transmission.

In addition, referring to FIG. 5, the physical sign detecting sleeve 221 may further include a signal transceiver 2213, for example, a cloud service signal transceiver, which may transmit detected physical sign information of a user to the telemedicine device through a cloud server.

By using the physical sign detecting sleeve in the embodiment of the present disclosure, the pulse information of the patient may be accurately and conveniently acquired, and may be transmitted to the telemedicine device at a remote location in real time.

In addition, referring to FIG. 4, the physiological sign information acquiring unit 220 may further include a fingerprint identifying unit 222, for acquiring fingerprint information of a patient, so that an identity of a user may be determined by the fingerprint information, and information such as historical case of the user may also be conveniently retrieved.

In addition, the physiological sign information acquiring unit 220 may further include an image acquiring unit, and the image acquiring unit is configured to acquire a body feature image of a patient. Optionally, the image acquiring unit may be a camera. For example, a rotatable camera is used, which may acquire images of various parts of a user at various angles. Of course, two cameras may be used, for example, a first camera and a second camera, the first camera is used for acquiring a half body or a whole body image of a patient, and the second camera is used for acquiring an image of a first part of the body of the patient. The camera may be rotated according to a user instruction, to acquire an image of specific part of the patient.

In addition, the physiological sign information acquiring unit 220 may further include a voice input device, configured for a patient to input a voice and have a voice dialogue with a doctor.

In addition, referring to FIG. 4, the physiological sign information acquiring unit 220 may further include a weight scale 223, to facilitate weighing a patient. In addition, when the physiological sign information acquiring unit 220 is a chair or a bed, a walking wheel 224 may be further provided under the chair or below the bed, to facilitate movement of a patient with inconvenient mobility.

By the telemedicine information acquiring device in the embodiment of the present disclosure, various physiological sign information of the user may be easily acquired through a simple configuration, and transmitted to the telemedicine device in real time, so as to save medical cost of the patient and improve user experience.

Figure 6:
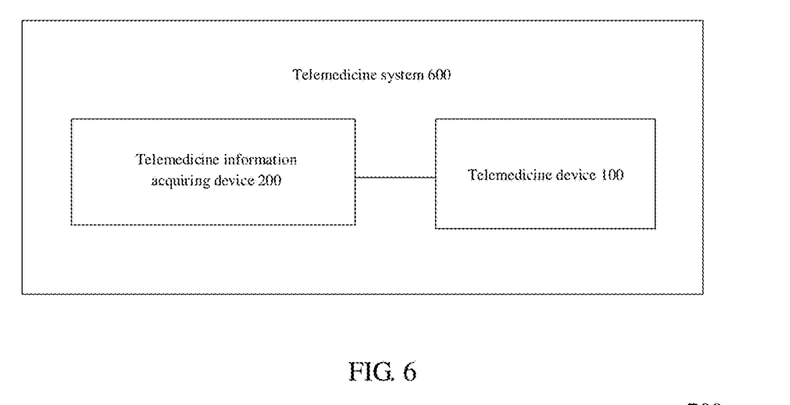
FIG. 6 shows an architectural diagram of a telemedicine system according to an embodiment of the present disclosure.

Hereinbefore, the telemedicine information acquiring device according to the embodiment of the present disclosure has been introduced. In addition, an embodiment of the present disclosure further provides a telemedicine system. FIG. 6 shows an architectural diagram of a telemedicine system according to an embodiment of the present disclosure. Referring to FIG. 6, the telemedicine system 600 comprises the telemedicine device 100 and the telemedicine information acquiring device 200 described above, and for the sake of brevity of the description, details are not repeated here and may be referred to the description of the foregoing embodiments.

Figure 7:
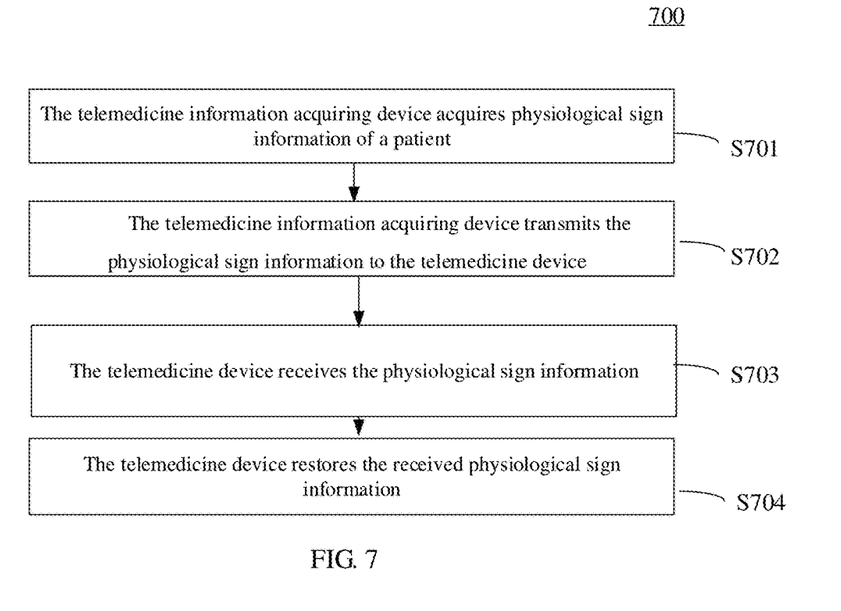
FIG. 7 shows a flowchart of a telemedicine method according to an embodiment of the present disclosure.

In addition, an embodiment of the present disclosure further provides a telemedicine method, which is an interacting method between the telemedicine device and the telemedicine information acquiring device described above. For the sake of brevity of the description, only a brief introduction is given in the following. FIG. 7 shows a flowchart of a telemedicine method according to an embodiment of the present disclosure. Referring to FIG. 7, the telemedicine method 700 may include steps as follows.

In step S701, the telemedicine information acquiring device acquires physiological sign information of a patient.

In step S702, the telemedicine information acquiring device transmits the physiological sign information to the telemedicine device.

In step S703, the telemedicine device receives the physiological sign information.

In step S704, the telemedicine device restores the received physiological sign information.

For example, the telemedicine information acquiring device acquires pulse information of a patient, and the telemedicine information acquiring device transmits a pulse signal indicating the pulse information to the telemedicine device. After receiving the pulse signal, the telemedicine device restores the received pulse signal to simulate the pulse information of the patient.

For another example, the telemedicine information acquiring device further acquires a body feature image of a patient and transmits the body feature image to the telemedicine device. The telemedicine device receives the body feature image and displays the received body feature image for viewing by the doctor.

In addition, the telemedicine information acquiring device may further acquires identity information of a patient and transmit the identity information to the telemedicine device. The telemedicine device receives the identity information and verifies an identity of the patient according to the received identity information.

The telemedicine method in the embodiment of the present disclosure may realize remote diagnosis in traditional Chinese medicine by interacting between the telemedicine device and the telemedicine information acquiring device, which improves efficiency of diagnosis, and facilitates use of a user.

Those of ordinary skilled in the art may appreciate that elements and algorithm steps in respective examples described in connection with the embodiments disclosed herein may be implemented in electronic hardware, computer software, or a combination of the two. And the software module may be placed in any form of computer storage medium. To clearly illustrate interchangeability of hardware and software, components and steps of the respective examples have been generally described in terms of functionality in the foregoing description. Whether these functions are performed in hardware or software depends on specific application and design constraints of technical solution. Those skilled in the art may use different methods to implement the described functions for each particular application, but such implementation should not be considered to be beyond the scope of the present disclosure.

Those skilled in the art should understand that, various modifications, combinations, partial combinations and substitutions of the present disclosure may be made depending on design requirements and other factors, as long as they are within the scope of the appended claims and their equivalents.

What is claimed is:

1. A telemedicine device, communicated with a telemedicine information acquiring device, the telemedicine device comprising: a communication unit and an operation unit,
    the communication unit being configured to communicate with the telemedicine information acquiring device, and receive physiological sign information of a patient from the telemedicine information acquiring device; and
    the operation unit being configured to restore at least part of the physiological sign information according to the physiological sign information received by the communication unit,
    wherein the operation unit includes a pulse restoring unit and the physiological sign information includes pulse information,
    the communication unit is further configured to receive a pulse signal indicating the pulse information of the patient from the telemedicine information acquiring device; and
    the pulse restoring unit is further configured to restore the pulse signal, so as to simulate pulse of the patient;
    wherein the pulse restoring unit includes a vibrating portion, the vibrating portion is configured to vibrate according to the received pulse signal, so as to simulate beating of the pulse of the patient;
    wherein the pulse restoring unit further includes a touch region, the touch region being provided with artificial human skin, the touch region is touched by a doctor for pulse diagnosis, so that the doctor senses the pulse signal indicating the pulse information of the patient.

2. The telemedicine device according to claim 1, wherein the vibrating portion is a Micro Electro Mechanical Systems based vibration sensor.

3. The telemedicine device according to claim 1, further comprising: a display unit,
    the communication unit receiving the pulse information of the patient from the telemedicine information acquiring device, and the display unit being configured to display a waveform diagram of the pulse information in the physiological sign information.

4. The telemedicine device according to claim 1, wherein the physiological sign information includes a body feature image,
    the communication unit being further configured to receive the body feature image of the patient from the telemedicine information acquiring device, and
    the display unit being configured to display the body feature image.

5. The telemedicine device according to claim 4, wherein the display unit includes a first display region and a second display region,
    the first display region being configured to display an overall image of the body feature image, and
    the second display region being configured to display an enlarged image of at least a part of the body feature image.

6. The telemedicine device according to claim 5, wherein the operation unit further includes a function switching device,
    the function switching device switching contents displayed by the first display region and the second display region according to a user instruction.

7. The telemedicine device according to claim 1, further comprising a speaker,
    the communication unit being further configured to receive sound information of the patient from the telemedicine information acquiring device, and
    the speaker being configured to output the sound information.

8. A telemedicine system, comprising the telemedicine device according to claim 1 and a telemedicine information acquiring device;
    the telemedicine information acquiring device, communicated with the telemedicine device, and the telemedicine information acquiring device including a communication unit and a physiological sign information acquiring unit;
    the physiological sign information acquiring unit being configured to acquire physiological sign information of the patient;
    the communication unit being configured to communicate with the telemedicine device, and transmit the physiological sign information to the telemedicine device.

9. The device according to claim 8, wherein the physiological sign acquiring unit includes a physical sign detecting sleeve, for being worn on a limb of the patient and acquiring pulse information of the patient.

10. The device according to claim 9, wherein the physical sign detecting sleeve includes a signal amplifier, configured to amplify a pulse signal indicating the pulse information.

11. The device according to claim 8, wherein the physiological sign information acquiring unit further includes a fingerprint identifying unit, configured to acquire fingerprint information of the patient.

12. The device according to claim 8, wherein the physiological sign information acquiring unit includes an image acquiring unit, the image acquiring unit being configured to acquire a body feature image of the patient.

13. The device according to claim 12, wherein the image acquiring unit includes a first camera and a second camera, the first camera being used for acquiring a half body or a whole body image of the patient, and the second camera being used for acquiring an image of a first part of the body of the patient.

14. The device according to claim 8, further comprising a voice input device, configured to input voice by the patient.

15. A telemedicine method, which is an interacting method between the telemedicine device according to claim 1 and a telemedicine information acquiring device, comprising:
   acquiring physiological sign information of a patient by a telemedicine information acquiring device;
   transmitting the physiological sign information to a telemedicine device by the telemedicine information acquiring device;
   receiving the physiological sign information by the telemedicine device; and
   restoring the received physiological sign information by the telemedicine device,
   wherein the physiological sign information comprises pulse information,
   the acquiring physiological sign information of a patient by a telemedicine information acquiring device comprises: acquiring the pulse information of the patient by the telemedicine information acquiring device;
   the transmitting the physiological sign information to the telemedicine device by the telemedicine information acquiring device comprises: transmitting a pulse signal indicating the pulse information to the telemedicine device by the telemedicine information acquiring device;
   the receiving the physiological sign information by the telemedicine device comprises: receiving the pulse signal by the telemedicine device;
   the restoring the received physiological sign information by the telemedicine device comprises: restoring the received pulse signal by the telemedicine device to simulate pulse of the patient; and
   the restoring the received pulse signal by the telemedicine device to simulate pulse of the patient comprises: vibrating according to the received pulse signal, so as to simulate beating of the pulse of the patient.

* * * * *